US 6,527,771 B1

(12) United States Patent
Weadock et al.

(10) Patent No.: US 6,527,771 B1
(45) Date of Patent: Mar. 4, 2003

(54) SURGICAL DEVICE FOR ENDOSCOPIC VEIN HARVESTING

(75) Inventors: Kevin S. Weadock, Princeton, NJ (US); Parris S. Wellman, Hillsborough, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/967,185

(22) Filed: Sep. 28, 2001

(51) Int. Cl.[7] .............................................. A61B 17/32
(52) U.S. Cl. ............................ 606/50; 606/48; 606/51; 606/170; 606/171
(58) Field of Search ............................ 606/41, 45, 46, 606/48–52, 170, 171, 159

(56) References Cited

U.S. PATENT DOCUMENTS

| 6,019,771 | A | | 2/2000 | Bennett et al. | |
|---|---|---|---|---|---|
| 6,022,313 | A | | 2/2000 | Ginn et al. | |
| 6,193,653 | B1 | * | 2/2001 | Evans et al. | 606/170 |
| 6,387,108 | B1 | * | 5/2002 | Taylor et al. | 606/170 |
| 6,436,116 | B1 | * | 8/2002 | Spitz et al. | 606/170 |
| 6,443,970 | B1 | * | 9/2002 | Schulze et al. | 606/171 |

* cited by examiner

Primary Examiner—Linda C. M. Dvorak
Assistant Examiner—David M. Ruddy

(57) ABSTRACT

A surgical device including: a first shaft having a first projection radially offset from an axial direction of the first shaft, the first projection having a first clamping surface; a second shaft slidably disposed relative to the first shaft, the second shaft having a second projection radially offset from the axial direction, the second projection having a second clamping surface; a dissector for dissecting tissue from a blood vessel to be harvested; a first actuator for sliding the second projection relative to the first projection to capture a side branch of the vessel between the first and second clamping surfaces; at least one electrode for applying cauterizing energy to cauterize the captured side branch; a cutting blade movably disposed on one of the first or second projections; and a second actuator for moving the cutting blade to sever the side branch captured between the first and second projections.

22 Claims, 4 Drawing Sheets

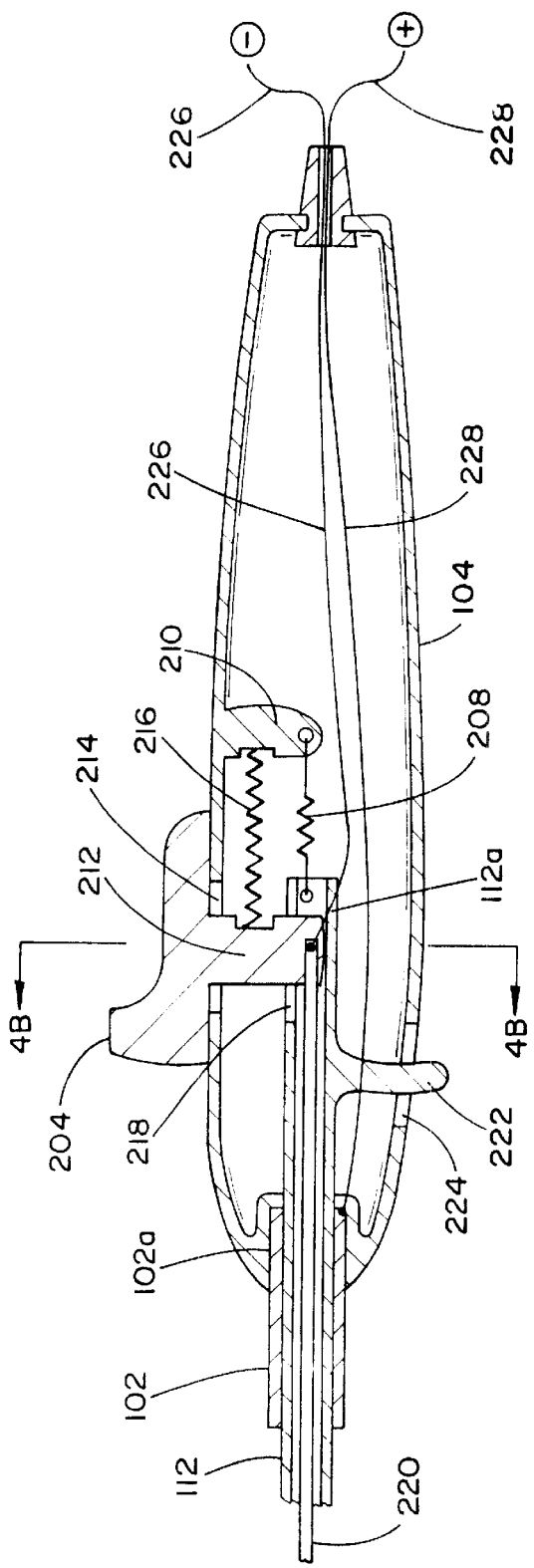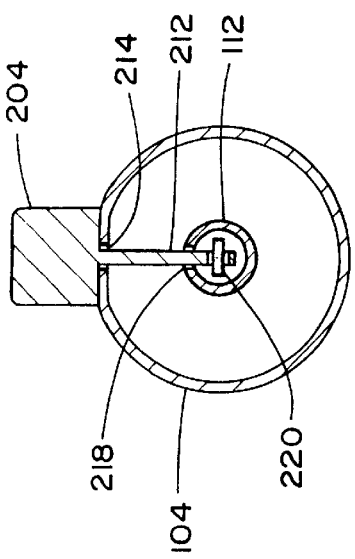
FIG. 4A
FIG. 4B

SURGICAL DEVICE FOR ENDOSCOPIC VEIN HARVESTING

BACKGROUND OF THE INVENTION

1. Field of the Invention

The present invention relates generally to surgical devices, and more particularly, to a surgical device for ligating and severing a side branch of a vessel to be harvested.

2. Prior Art

Both saphenous veins and radial arteries are used as conduits in coronary artery bypass surgery. Conventional techniques for harvesting these vessels involve an incision length approximately equal to the length of the vessel being harvested. Recently, various bipolar endoscopic vessel harvesting devices have been developed as a means of removing saphenous veins or radial arteries in a minimally invasive manner.

Users of theses devices frequently struggle to separate side branches of the veins or arteries when said side branches run beneath or above the main trunk of the vessel. In addition, the visualization of the vessel may be lost in excess adipose tissue. Finally, the user friendliness of these devices is subject to question since the steps involved in identifying, securing, and dissection/ligation of side branches is not always intuitive, i.e., the user frequently has to concentrate on what his or her hands are doing and not the vessel at hand. Current bipolar devices also fail to complete the terminal ligation required to excise the vein or artery.

Others have attempted to harvest vessels via endoscopic means by several methods. One method involves use of scissors and ligating clips. Two tools are required for this approach, thus complicating the procedure by excess tool exchanges. Furthermore, the placed clips can hinder subsequent movement of instruments. Finally, foreign bodies (clips) are left in the patient's limb.

Another approach involves the use of a knife placed between two wire guides that are capable of applying a current across the side branch. This design can potentially result in the spread of thermal energy to the target vessel, potentially compromising its utility as a conduit for CABG surgery. Still yet another approach involves the use of scissor-like clamping jaws that open around a side branch, and then must be closed, whereby a current is applied to the vessel within the jaws before the vessel is harvested. The movement of the jaws is frequently hindered by surrounding tissue or by an endoscopic spoon used to provide visualization.

SUMMARY OF THE INVENTION

Therefore it is an object of the present invention to provide a surgical device for endoscopic vessel harvesting which is friendlier to use than conventional endoscopic vessel harvesting devices.

It is another object of the present invention to provide a surgical device for endoscopic vessel harvesting which eliminates the need for ligating clips to ligate side branches of a vessel being harvested.

It is yet another object of the present invention to provide a surgical device for endoscopic vessel harvesting which limits the spread of thermal energy so as not to compromise the utility of the vessel to be harvested.

It is yet another object of the present invention to provide a surgical device for endoscopic vessel harvesting which eliminates the necessity of opening and closing scissor-like jaws around a side branch to ligate the same.

It is still yet another object of the present invention to provide a surgical device for endoscopic vessel harvesting which minimizes the need for multiple instrument exchanges needed to harvest a vessel.

Accordingly, a surgical device is provided. The surgical device comprises: a first shaft having a first projection radially offset from an axial direction of the first shaft, the first projection having a first clamping surface; a second shaft slidably disposed relative to the first shaft, the second shaft having a second projection radially offset from the axial direction, the second projection having a second clamping surface; first actuation means for sliding the second projection relative to the first projection to capture a vessel between the first and second clamping surfaces; at least one electrode for applying cauterizing energy to cauterize the captured vessel; a cutting blade movably disposed on one of the first or second projections; and second actuation means for moving the cutting blade to sever the vessel captured between the first and second projections. Preferably, the vessel captured, cauterized, and severed is a side branch of a blood vessel being harvested.

Preferably, the first and second projections are offset from the axial direction of the first and second shafts, respectively, at an angle of about 90 degrees.

The surgical device preferably further comprises a handle, wherein a proximal end of the first shaft is fixed to the handle and the first actuation means comprises a button movably disposed in the handle, wherein movement of the button slides the second projection relative to the first projection. When so configured, the surgical device preferably further comprises: biasing means for biasing the first and second projections together such that the first and second clamping surfaces are in substantial contact; a control rod operatively connected at a proximal end to the button and at a distal end to the cutting blade, wherein the control rod is disposed in a lumen of the first shaft; wherein the second projection is slid relative to the first projection by actuating the cutting blade to act against the second clamping surface to spread the second and first projections apart.

Preferably, the surgical device further comprises a handle, wherein a proximal end of the first shaft is fixed to the handle, the cutting blade is disposed in the second projection, and the second actuation means comprises a button movably disposed in the handle, wherein movement of the button moves the cutting blade to sever the vessel. When so configured, the surgical device further comprises a control rod operatively connected at a proximal end to the button and at a distal end to the cutting blade, wherein the control rod is disposed in a lumen of the first shaft.

The surgical device also preferably further comprises a dissection means for dissecting tissue from a blood vessel to be harvested. The dissection means preferably comprises a third shaft having an internal lumen for passage of an endoscope therein, the dissection means further having a headpiece shaped for dissecting tissue. When so configured, the surgical device further comprises a handle, wherein the third shaft and the first shaft are arranged parallel and each are connected at a proximal end to the handle.

Preferably, the cauterizing energy is radio-frequency energy supplied to the at least one electrode. Alternatively, the cauterizing energy can be sonic energy supplied to the at least one electrode. The at least one electrode preferably comprises a first electrode of a first polarity and a second electrode of a second polarity opposite from the first polarity, the first electrode being disposed on the first clamping surface and the second electrode being disposed on one of the second clamping surface and cutting blade, preferably, on the cutting blade.

The surgical device also preferably further comprises alignment means for maintaining alignment of the first and second clamping surfaces.

Also provided is a surgical device for endoscopic vein harvesting. The device comprising: a first shaft having a first projection radially offset from an axial direction of the first shaft, the first projection having a first clamping surface; a second shaft slidably disposed relative to the first shaft, the second shaft having a second projection radially offset from the axial direction, the second projection having a second clamping surface; a dissection means for dissecting tissue from a blood vessel to be harvested; first actuation means for sliding the second projection relative to the first projection to capture a side branch of the vessel between the first and second clamping surfaces; at least one electrode for applying cauterizing energy to cauterize the captured side branch; a cutting blade movably disposed on one of the first or second projections; and second actuation means for moving the cutting blade to sever the side branch captured between the first and second projections.

The dissection means of the surgical device for endoscopic vein harvesting preferably comprises a third shaft having an internal lumen for passage of an endoscope therein, the dissection means further having a headpiece shaped for dissecting tissue in proximity to the vessel. When so configured, the surgical device further comprises a handle, wherein the third shaft and the first shaft are arranged parallel and each are connected at a proximal end to the handle.

Still yet provided is a method for severing a side branch of a vessel. The method comprises: providing the surgical device; positioning the surgical instrument over the vessel; positioning the first and second projections around the side branch; sliding the second shaft to capture the side branch between the first and second clamping surfaces; applying a cauterizing energy to the first and second electrodes to cauterize the captured side branch; and moving the cutting blade to sever the side branch captured between the first and second projections.

The sliding step preferably comprises actuating a button movably disposed in a handle on the surgical instrument, wherein actuation of the button slides the second projection relative to the first projection. The moving step preferably comprises actuating a button movably disposed in a handle of the surgical instrument, wherein movement of the button moves the cutting blade to sever the side branch.

The method preferably also further comprises dissecting tissue from around the vessel to expose the side branch. The positioning of the first and second projections around the side branch preferably comprises rotating the surgical instrument about the axial direction.

BRIEF DESCRIPTION OF THE DRAWINGS

These and other features, aspects, and advantages of the apparatus and methods of the present invention will become better understood with regard to the following description, appended claims, and accompanying drawings where:

FIG. 4a illustrates a sectional view taken along line 4a—4a in FIG. 1.

FIG. 4b illustrates a sectional view taken along line 4b—4b in FIG. 4a.

DETAILED DESCRIPTION OF THE PREFERRED EMBODIMENT

Although this invention is applicable to numerous and various types of vessels to be severed, it has been found particularly useful in the environment of severing side branches of a blood vessel being harvested. Therefore, without limiting the applicability of the invention to severing side branches of a blood vessel being harvested, the invention will be described in such environment. Furthermore, the surgical devices of the present invention is preferably configured as a disposable device, however, the surgical devices can also be configured as semi-reusable or reusable without departing from the scope or spirit of the present invention.

Figure 1:
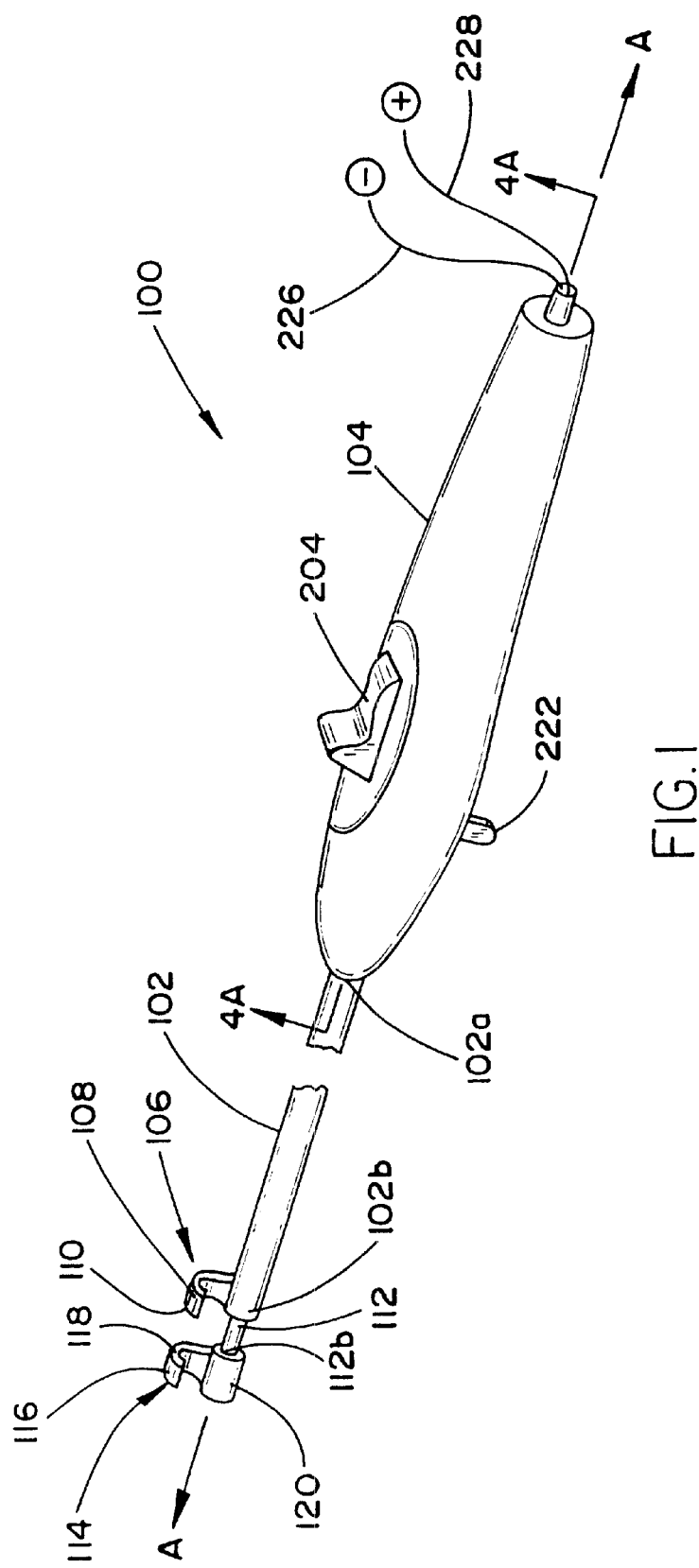
FIG. 1 illustrates an isometric view of a preferred implementation of the surgical device of the present invention.
Figure 2:
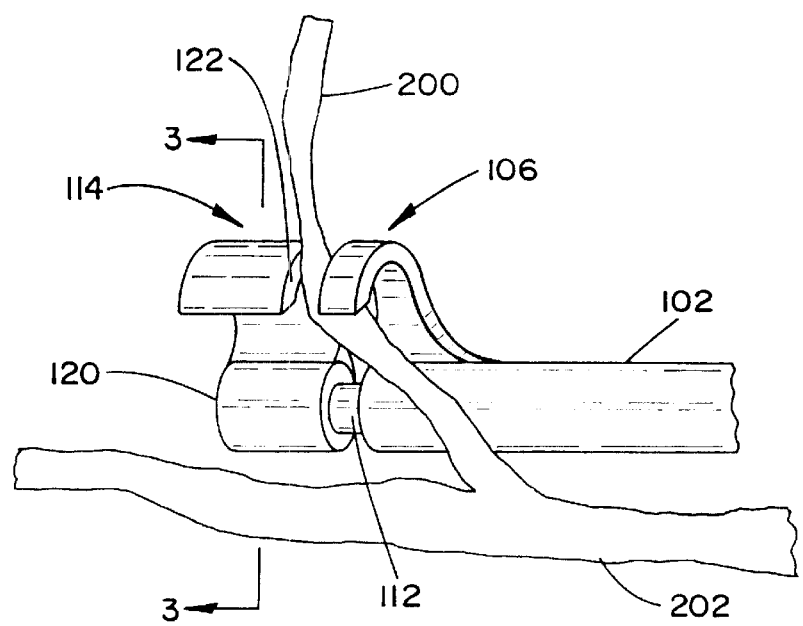
FIG. 2 illustrates a side branch vessel captured between two radially offset projections on a distal end of the surgical device of FIG. 1.

Referring now to FIGS. 1 and 2, a surgical device is illustrated therein, generally being referred to by reference numeral 100. The surgical device 100 has a first shaft 102. The first shaft 102 is preferably fabricated from a resilient medical grade material, such as stainless steel tubing having at least one internal lumen. The first shaft 102 is fixed to a housing 104 at a distal end 102a. The housing 104 also preferably serves as a handle for manipulation of the surgical device 100. The first shaft 102 is fixed to the housing 104 by any means known in the art such as by a press fit or with a medical grade epoxy. The first shaft 102 further has a first projection 106 disposed at a distal end 102b.

The first projection is radially offset from an axial direction A of the first shaft 102. The first projection 106 is preferably hook shaped and having a hook portion 108. The first projection 106 also has a first clamping surface 110, preferably on a distal end of the hook portion 108. The first projection is preferably fabricated from a resilient medical grade material such as stainless steel and is preferably disposed on the first shaft 102 by welding or brazing.

The surgical device 100 also has a second shaft 112 slidably disposed relative to the first shaft 102. Preferably, the second shaft 112 is slidingly disposed in the lumen of the first shaft 102. The second shaft is preferably fabricated from a resilient medical grade material, such as stainless steel tubing having at least one internal lumen 113.

The second shaft also has a second projection 114 disposed at a distal end 112b. Like the first projection 106, the second projection 114 is also radially offset from the axial direction A. The second projection 114 is preferably hook shaped and has a hook portion 116. The second projection 114 also has a second clamping surface 118, preferably on a proximal end of the hook portion 116. The hook portion 116 and second clamping surface 118 of the second projection 114 preferably correspond to the hook portion 108 and first clamping surface 110 of the first projection 106 such that when the second shaft 112 is slid proximally, the first and second clamping surfaces 110, 118 coincide.

The first and second projections 106, 114 are preferably offset from the axial direction A of the first and second shafts 102, 112, respectively, at an angle of about 90 degrees. However, a 90-degree offset is given by way of example only and not to limit the scope or spirit of the present invention. For instance, a 45-degree offset may also be used without departing from the scope or spirit of the present invention.

The second projection is preferably fabricated from a resilient medical grade material such as stainless steel and is preferably disposed on the second shaft 112 by welding or brazing. More preferably, the second projection 114 is disposed on a sleeve 120 which itself is disposed on the distal end 112b of the second shaft 112, preferably by welding or brazing. However, the sleeve can also be epoxied or press fit to the distal end 112b of the second shaft 112.

Figure 3:
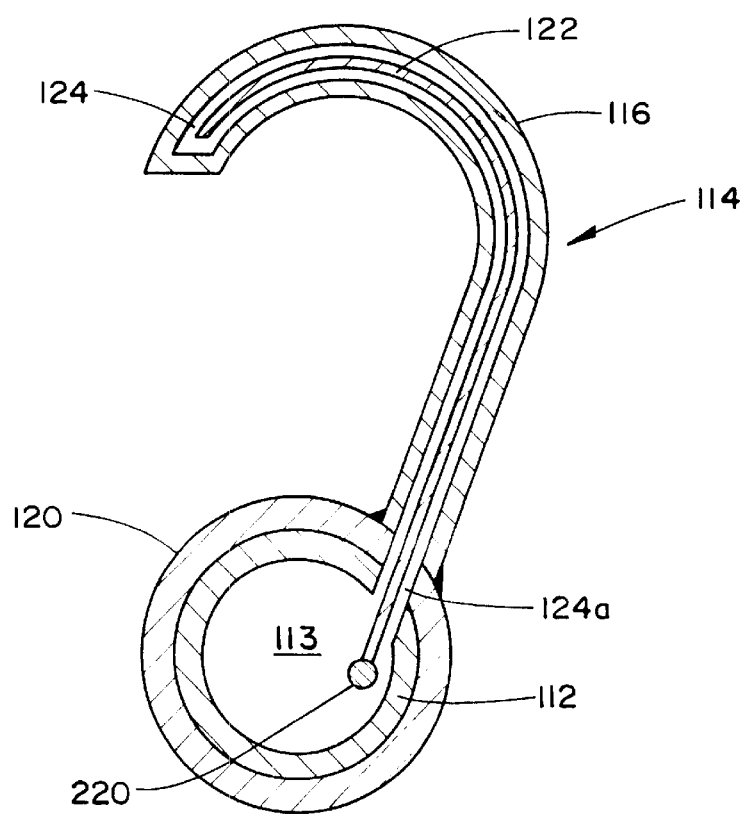
FIG. 3 illustrates a sectional view taken along line 3—3 in FIG. 2.

Referring now to FIGS. 2 and 3, a cutting blade 122 is movably disposed on one of the first or second projections 106, 114. Preferably, the cutting blade 122 is disposed on the second projection 114. More preferably, the cutting blade 122 is disposed in a corresponding slot 124 in the second clamping surface 118 and mimics the shape of the hook portion 116 of the second projection 114. The cutting blade 122 preferably has a sharpened edge facing the first clamping surface 110 of the first projection 106. The cutting edge 122 is preferably fabricated from a resilient medical grade material, which is treated to maintain the sharpened edge from dulling. Preferably, the cutting blade 122 is fabricated from a heat treatable stainless steel and at least the sharpened edge is heat treated to prevent the sharpened edge from dulling within the expected lifetime of the device 100.

A first actuation means is provided for sliding the second projection 114 relative to the first projection 106 to capture a vessel 200 between the first and second clamping surfaces 106, 118. Furthermore, a second actuation means is also provided for moving the cutting blade 122 to sever the captured vessel 200. The captured vessel 200 is preferably a side branch of a blood vessel 202 being harvested.

Referring additionally to FIGS. 4A and 4B, preferably, the first actuation means comprises a button 204 movably disposed in the handle 104, wherein movement of the button 204 slides the second projection 114 relative to the first projection 106. Preferably, second shaft 112 is biased in the proximal direction to bias the first and second clamping surfaces 110, 118 together. The second shaft 112 is preferably biased in such as manner by way of an extension spring 208 disposed between a handle projection 210 on an interior of the handle 104 and a proximal end 112a of the second shaft 112.

The button 204 is slidingly engaged with the handle 104 by way of a button projection 212 disposed in a slot 214 in the handle 104. The button 204 is preferably biased in the distal direction by a compression spring 216 disposed between the handle projection 210 and the button projection 212. The button projection 212 is preferably further disposed in a corresponding slot 218 disposed in the proximal end 112a of the second shaft 112. A control rod 220, disposed in the lumen 113 of the second shaft 112 is connected at a proximal end to the button 204 and at a distal end to the cutting blade 122.

The cutting blade 122 preferably has a projection 122a, which could be integral with the cutting blade 122 or a separately attached piece, which enters the lumen 113 of the second shaft 112 by way of an extension 124a of slot 124 to connect to the control rod 220. The connection between the control rod 220 and the projection 122a of the cutting blade 122 is preferably made by way of a pinned joint.

To separate the first and second projections 106, 114, the button 204 is slid proximally against the biasing force of the compression spring 216 to slide the cutting blade 122 in the slot 124 and to urge the cutting blade 122 against the first clamping surface 110. This results in the separation of the first and second projections 106, 114. Once separated, the second shaft 112 is held in place while the surgical device 100 is manipulated to capture the vessel 200 between the first and second projections 106, 114 as is shown in FIG. 2. The second shaft 102 is then allowed to slide proximally to clamp the vessel 200 between the first and second clamping surfaces 110, 118. After cauterization of the captured vessel 200 (discussed below), the button 204 is again slid proximally to slide the cutting blade 122 to sever the vessel 200.

The means for holding the second shaft 102 in place while the vessel 200 is captured preferably comprises a shaft projection 222 connected to the second shaft 102 and projecting from a corresponding slot 224 in the handle 104 where the shaft projection 222 is held manually by the surgeon to hold the second shaft 102 and released to allow the second shaft 102 to slide proximally. The shaft projection 222 and slot 224 further preferably comprises alignment means for maintaining alignment of the first and second clamping surfaces 110, 118. That is, relative rotation of the first and second shafts 102, 112 is prevented by the shaft projection 222.

Those skilled in the art will appreciate that many different actuation means for sliding the second shaft 112 and moving the cutting blade 122 are possible and can be employed without departing from the scope or spirit of the present invention. For instance, two buttons can be provided, one of which is operatively connected to the second shaft 112 to slide the same axially along axis A, the other of which is operatively connected to the cutting blade 122 to move the same in the slot 124 in the axial direction.

The surgical device 100 of the present invention also includes at least one electrode for applying cauterizing energy to cauterize the captured vessel 200 between the first and second clamping surfaces 110, 118. Preferably, the surgical device 100 is configured to apply RF energy to cauterize the captured vessel 200 and more preferably, the surgical device 100 is further configured as a bipolar device. However, the preferable means for cauterization is given by way of example only and not to limit the scope or spirit of the present invention. For instance, the surgical device 100 can be used in a monopolar configuration in combination with a grounding plate as is known in the art. Furthermore, the surgical device 100 can be configured to apply sonic energy to cauterize the captured vessel 200.

In the preferred bipolar configuration, the first clamping surface 110 acts as a first electrode of a first polarity and the cutting blade 122 acts as a second electrode of a second polarity, opposite from the first polarity. Alternatively, the second clamping surface 118 can be utilized as the second electrode. The RF energy is preferably supplied from an electrosurgical generator (not shown), as is known in the art. A switch (not shown) is also preferably provided for energizing the electrodes with RF energy from the electrosurgical generator. The switch can be provided in the handle 104 or in a foot switch (not shown) as are known in the art.

The conductive path from the electrosurgical generator to the electrodes preferably comprise wires 226, 228 connected at a proximal end to the electrosurgical generator and at distal ends to their respective electrodes. Preferably, wire 226 is connected to the control rod, which supplies the RF energy to the cutting blade 122. Similarly, wire 228 is preferably connected to the distal end 102a of the first shaft 102 to supply RF energy to the first clamping surface 110 of the first projection 106. In such a configuration, surfaces such as the exterior of the first and second shafts 102, 112, the control rod 220, and the slot 124 must be coated with a dielectric material to prevent a short between the electrodes of different polarity and also to prevent accidental cauterization of unintended tissue. Such coatings are well known in the art, such as polytetrafluorethylene (PTFE). Surfaces of the first and second projections 106, 114, other than the first and second clamping surfaces 110, 118 may also be coated with the dielectric material.

Preferably, the surgical device further has a means (not shown) for evacuating smoke or other fluids from the body. Typically, the evacuating means comprises a vacuum port (not shown) such as a luer fitting disposed in the handle 104, which is in fluid communication with the lumen 113 at one end and connected to a vacuum supply at another end.

Figure 5:
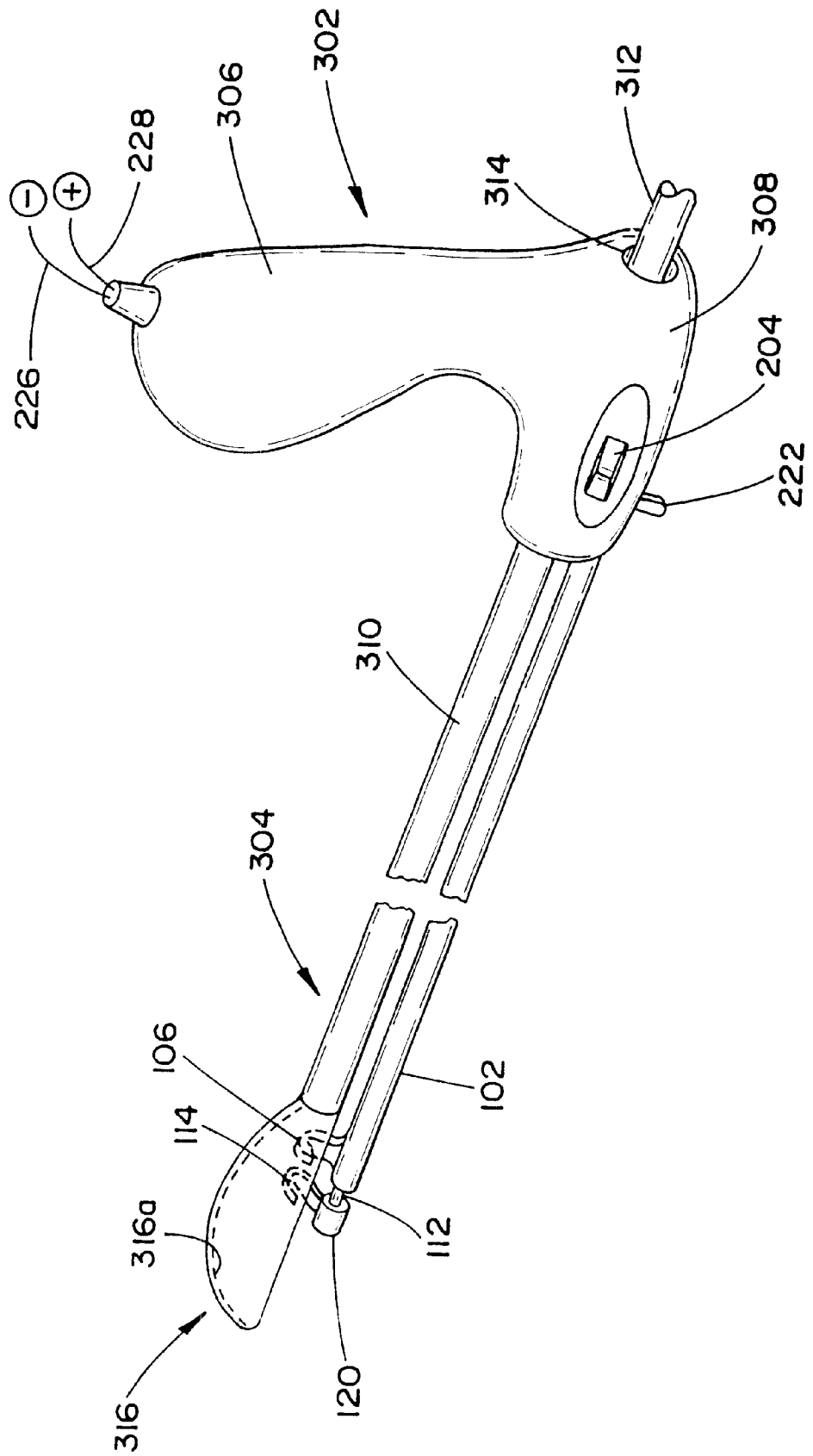
FIG. 5 illustrates a dissection tool having a variation of the surgical device of FIG. 1 integrated therein.

Referring now to FIG. 5 where like numbers represent similar components, a variation of the surgical device 100 is illustrated therein. The variation of the surgical device being generally referred to by reference numeral 300. The surgical device 300 illustrated in FIG. 5 is similar to the surgical device 100 illustrated in FIG. 1, but is particularly configured for endoscopic vein harvesting.

The device 300 comprises a substantially similar instrument as disclosed in FIGS. 1, 2, 3, 4A, and 4B, with the exception that the housing 302 is configured as is known in the art for blood vessel dissection and the addition of a dissection means 304 for dissecting tissue from a blood vessel to be harvested. The housing 302 of surgical device 300 is pistol or L-shaped and has a handle portion 306. The housing 302 also has a control portion 308 for placement of the button 204 and shaft projection 222 as well being a housing for the remaining components of the first and second actuation means discussed previously with regard to surgical device 100.

The dissection means 304 preferably comprises a third shaft 310 having an internal lumen for passage of an endoscope 312 therein. The internal lumen communicates with a lumen (not shown) in the handle and has a hole 314 for insertion of the endoscope therein. The third shaft 310 and the first shaft 102 are preferably arranged parallel to one another and each are connected at a proximal end to the control portion 308 of the housing 302.

The dissection means 304 further has a substantially transparent headpiece 316 shaped for dissecting tissue in proximity to the vessel 202. Dissecting tissue about a vessel 202 with such a dissection means 304 is well known in the art, such as that disclosed in U.S. Pat. No. 6,206,823, the contents of which are incorporated herein by its reference. In general, the headpiece 316 is advanced along the vessel 202 to dissect the surrounding tissue from the vessel 202. Furthermore, a workspace is created between an interior surface 316a of the headpiece 316 and the vessel 202 for placement of the first and second projections 106, 114. If a side branch 200 of the vessel 202 is encountered during the dissection (as viewed by the endoscope), the same is ligated and dissected in the workspace using the first and second projections 106, 114.

A method for severing a side branch 200 of a vessel 202 using the surgical devices 100, 300 of the present invention will now be described with reference to the Figures. A vessel 202 to be harvested is first accessed by making an incision, generally in the leg. Next, pre-dissection of an end of the vessel 202 is performed. After pre-dissection, the vessel 202 is traversed and dissected from the surrounding tissue. During the dissection of the vessel 202, whenever a side branch 200 is encountered, the first and second projections 106, 114 are positioned around the side branch 200. To position the first and second projections 106, 114 around the side branch 202, the first and second projections 106, 114 are separated as discussed above and the shaft projection 222 is held to maintain them in the separate position. Since the first and second projections 106, 114 are radially offset from the axis A, which is generally parallel with the axis of the vessel 202, the positioning of the first and second projections 106, 114 around the side branch 202 preferably comprises rotating the surgical device 100, 300 about the axial direction A until the side branch 202 is positioned between the first and second projections 106, 114.

Once the side branch 202 is positioned, the second shaft 102 is slid proximally to capture the same between the first and second clamping surfaces 110, 118 of the first and second projections 106, 114. Preferably, the second shaft 102 is slid proximally by releasing the shaft projection 222 thereby allowing the biasing force of the extension spring 208 to bias the second shaft 102 in the proximal direction.

Once the side branch 200 is captured, a cauterizing energy is applied to the electrodes to cauterize and ligate the captured side branch 202. As discussed above, the application of cauterizing energy is achieved by activating a switch on the device or a foot switch connected thereto. Subsequent to ligation by cauterization, the side branch 200 can then be severed. Preferably, the side branch 200 is severed by moving the cutting blade 122 proximally with button 204.

The process continues until an appropriate length of vessel 202 is traversed and all its side branches 200 are ligated and transected. The vessel 202 is then removed by transecting its ends.

EXAMPLE

As discussed above, the present invention has particular utility in a coronary artery bypass graft procedure (CABG), however, the use of the instruments of the present invention is now described with regard to the CABG procedure by way of example only and not to limit the scope or spirit of the present invention. A patient is prepared for cardiac surgery in a conventional manner using conventional techniques and procedures. The patient is then anesthetized and ventilated using conventional techniques. A conventional CABG procedure is performed by harvesting the greater saphenous vein from one or both of the patient's legs. The surgeon prepares an opening to the heart by dividing the patient's sternum (conventional median sternotomy) and spreading the rib cage apart using a surgical retractor. The surgeon next begins dissecting the internal mammary artery (IMA) from the chest wall of the patient, so that the distal end of the vessel may be anastomosed to the diseased lower anterior descending (LAD) coronary artery on the distal side of a lesion on the septum near the left ventricle of the heart as a source of oxygenated blood. During the surgical procedure, the surgeon optionally elects to have the patient's heart beating to perform a conventional beating heart CABG, although the surgeon has a cardiopulmonary bypass machine (CPB) primed with the patient's blood and available if it is necessary to convert the beating heart procedure into a conventional stopped heart procedure.

The surgeon prepares the heart for attaching the graft vessels by cutting and pulling away the pericardium. After checking the graft vessels for patency, collateral damage and viability, the surgeon prepares to do the anastomoses necessary to bypass the lesions in the coronary arteries. The surgeon sutures the proximal end of each graft vessel to the patient's aorta and the distal end to the diseased coronary artery, distal to the blockage or lesion. The distal end of the LAD is similarly anatomosed to a coronary artery distal to a lesion in a conventional manner. The surgeon checks the bypass grafts for adequate blood flow in a conventional manner, and then completes the remainder of the operation in a conventional manner.

The veins used in the CABG procedure are harvested endoscopically using the surgical instruments of the present invention. Using these instruments, initially the patient's leg is positioned to be slightly bent and is turned to expose the inner leg. A marker is used to show on the skin the location of the vein to be harvested. Then an incision is created on the inner leg near the knee, through the skin and subcutaneous layers. The vein typically lies directly beneath the subcutaneous layers and so a middle portion of the vein is accessed through the incision. After some initial dissection with conventional blunt dissectors around this portion of the vein, a surgical instrument is introduced into the incision. An endoscope provides visualization of the vein and surrounding tissue within the working space inside the head. The instrument is advanced along the vein. Side branches off of the vein are ligated and divided a few millimeters away from the vein, taking great care not to injure the vein in any way. The harvesting procedure continues in this manner until the vein is hemostatically isolated from surrounding tissues and blood supply along the portion to be harvested. Then stab incisions are created through the skin and subcutaneous layers at the distal and proximal ends of the vein, ligation clips are applied, and the vessel is transected in order to remove the vein from the knee incision. Thee harvested vein is prepared for use as grafts in a conventional manner.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A surgical device comprising:
    a first shaft having a first projection radially offset from an axial direction of the first shaft, the first projection having a first clamping surface;
    a second shaft slidably disposed relative to the first shaft, the second shaft having a second projection radially offset from the axial direction, the second projection having a second clamping surface;
    first actuation means for sliding the second projection relative to the first projection to capture a vessel between the first and second clamping surfaces;
    at least one electrode for applying cauterizing energy to cauterize the captured vessel;
    a cutting blade movably disposed on one of the first or second projections; and
    second actuation means for moving the cutting blade to sever the vessel captured between the first and second projections.

2. The surgical device of claim 1, wherein the first and second projections are offset from the axial direction of the first and second shafts, respectively, at an angle of about 90 degrees.

3. The surgical device of claim 1, further comprising a handle, wherein a proximal end of the first shaft is fixed to the handle and the first actuation means comprises a button movably disposed in the handle, wherein movement of the button slides the second projection relative to the first projection.

4. The surgical device of claim 3, further comprising:
    biasing means for biasing the first and second projections together such that the first and second clamping surfaces are in substantial contact;
    a control rod operatively connected at a proximal end to the button and at a distal end to the cutting blade, wherein the control rod is disposed in a lumen of the first shaft;
    wherein the second projection is slid relative to the first projection by actuating the cutting blade to act against the second clamping surface to spread the second and first projections apart.

5. The surgical device of claim 1, further comprising a handle, wherein a proximal end of the first shaft is fixed to the handle, the cutting blade is disposed in the second projection, and the second actuation means comprises a button movably disposed in the handle, wherein movement of the button moves the cutting blade to sever the vessel.

6. The surgical device of claim 5, further comprising a control rod operatively connected at a proximal end to the button and at a distal end to the cutting blade, wherein the control rod is disposed in a lumen of the first shaft.

7. The surgical device of claim 1, further comprising a dissection means for dissecting tissue from a blood vessel to be harvested.

8. The surgical device of claim 7, wherein the dissection means comprises a third shaft having an internal lumen for passage of an endoscope therein, the dissection means further having a headpiece shaped for dissecting tissue.

9. The surgical device of claim 8, further comprising a handle, wherein the third shaft and the first shaft are arranged parallel and each are connected at a proximal end to the handle.

10. The surgical device of claim 1, wherein the vessel captured, cauterized, and severed is a side branch of a blood vessel being harvested.

11. The surgical device of claim 1, wherein the cauterizing energy is radio-frequency energy supplied to the at least one electrode.

12. The surgical device of claim 1, wherein the cauterizing energy is sonic energy supplied to the at least one electrode.

13. The surgical device of claim 1, wherein the at least one electrode comprises a first electrode of a first polarity and a second electrode of a second polarity opposite from the first polarity, the first electrode being disposed on the first clamping surface and the second electrode being disposed on one of the second clamping surface and cutting blade.

14. The surgical device of claim 1, further comprising alignment means for maintaining alignment of the first and second clamping surfaces.

15. A method for severing a side branch of a vessel, the method comprising:
    providing a surgical device comprising: a first shaft having a first projection radially offset from an axial direction of the first shaft, the first projection having a first clamping surface; a second shaft slidably disposed relative to the first shaft, the second shaft having a second projection radially offset from the axial direction, the second projection having a second clamping surface; first actuation means for sliding the second projection relative to the first projection to capture a vessel between the first and second clamping surfaces; at least one electrode for applying cauterizing energy to cauterize the captured vessel; a cutting blade movably disposed on one of the first or second projections; and second actuation means for moving the cutting blade to sever the vessel captured between the first and second projections;

positioning the surgical instrument over the vessel;

positioning the first and second projections around the side branch;

sliding the second shaft to capture the side branch between the first and second clamping surfaces;

applying a cauterizing energy to the first and second electrodes to cauterize the captured side branch; and moving the cutting blade to sever the side branch captured between the first and second projections.

16. The method of claim 15, wherein the sliding step comprises actuating a button movably disposed in a handle on the surgical instrument, wherein actuation of the button slides the second projection relative to the first projection.

17. The method of claim 15, wherein the moving step comprises actuating a button movably disposed in a handle of the surgical instrument, wherein movement of the button moves the cutting blade to sever the side branch.

18. The method of claim 15, further comprising dissecting tissue from around the vessel to expose the side branch.

19. The method of claim 15, wherein the positioning of the first and second projections around the side branch comprises rotating the surgical instrument about the axial direction.

20. A surgical device for endoscopic vein harvesting, the device comprising:

a first shaft having a first projection radially offset fro an axial direction of the first shaft, the first projection having a first clamping surface;

a second shaft slidably disposed relative to the first shaft, the second shaft having a second projection radially offset from the axial direction, the second projection having a second clamping surface;

a dissection means for dissecting tissue from a blood vessel to be harvested;

first actuation means for sliding the second projection relative to the first projection to capture a side branch of the vessel between the first and second clamping surfaces;

at least one electrode for applying cauterizing energy to cauterize the captured side branch;

a cutting blade movably disposed on one of the first or second projections; and second actuation means for moving the cutting blade to sever the side branch captured between the first and second projections.

21. The surgical device of claim 20, wherein the dissection means comprises a third shaft having an internal lumen for passage of an endoscope therein, the dissection means further having a headpiece shaped for dissecting tissue in proximity to the vessel.

22. The surgical device of claim 21, further comprising a handle, wherein the third shaft and the first shaft are arranged parallel and each are connected at a proximal end to the handle.

* * * * *